(12) United States Patent
Keidar et al.

(10) Patent No.: US 10,213,614 B2
(45) Date of Patent: *Feb. 26, 2019

(54) SYSTEM AND METHOD FOR COLD PLASMA THERAPY

(75) Inventors: Michael Keidar, Baltimore, MD (US); Charanjeet Guron, Edina, MD (US); Barry Trink, Baltimore, MD (US); Alexey Shashurin, Rockville, MD (US)

(73) Assignee: U.S. Patent Innovations, LLC, Takoma Park, MD (US)

( * ) Notice: Subject to any disclaimer, the term of this patent is extended or adjusted under 35 U.S.C. 154(b) by 98 days.

This patent is subject to a terminal disclaimer.

(21) Appl. No.: 14/365,478

(22) PCT Filed: Jun. 1, 2012

(86) PCT No.: PCT/US2012/040474
§ 371 (c)(1),
(2), (4) Date: Jun. 13, 2014

(87) PCT Pub. No.: WO2012/167089
PCT Pub. Date: Dec. 6, 2012

(65) Prior Publication Data
US 2014/0378892 A1    Dec. 25, 2014

(51) Int. Cl.
| *A61B 18/14* | (2006.01) |
| *A61N 1/44* | (2006.01) |
| *A61B 18/04* | (2006.01) |
| *A61B 18/00* | (2006.01) |

(52) U.S. Cl.
CPC .............. *A61N 1/44* (2013.01); *A61B 18/042* (2013.01); *A61B 2018/00583* (2013.01)

(58) Field of Classification Search
CPC ................ A61B 18/14; A61B 18/042; A61B 2018/00589; A61B 2018/00607; A61B 2018/00583; A61N 1/44
See application file for complete search history.

(56) References Cited

U.S. PATENT DOCUMENTS 3,838,242 A * 9/1974 Goucher .............. A61B 18/042
128/908
3,903,891 A * 9/1975 Brayshaw ................ H05H 1/30
313/231.31
6,099,523 A * 8/2000 Kim ..................... A61B 18/042
606/40
(Continued)

FOREIGN PATENT DOCUMENTS

WO    03028542    4/2003

*Primary Examiner* — Michael Peffley
(74) *Attorney, Agent, or Firm* — 24IP Law Group; Timothy R Dewitt (57) ABSTRACT

A device uses cold plasma to treat cancerous tumors. The device has a gas supply tube with a delivery end. The gas supply tube is configured to carry a gas to the delivery end. A syringe is provided having an opening. The syringe is connected to the supply tube and configured to carry the gas to the opening. A first electrode is positioned inside said syringe, and a second electrode is positioned adjacent to the opening. The first and second electrodes excite the gas to enter a cold plasma state prior to being discharged from the opening of the syringe. An endoscopic tube can be used instead of the syringe. An exhaust tube can be provided to remove gas introduced into the body cavity by the cold plasma jet.

13 Claims, 4 Drawing Sheets

(56) References Cited

U.S. PATENT DOCUMENTS

| | | | |
|---|---|---|---|
| 6,890,332 B2* | 5/2005 | Truckai | A61B 17/22004 |
| | | | 128/898 |
| 6,958,063 B1* | 10/2005 | Soli | A61B 18/042 |
| | | | 606/32 |
| 2007/0029500 A1 | 2/2007 | Coulombe | |
| 2011/0112528 A1* | 5/2011 | Stieber | A61L 2/0011 |
| | | | 606/41 |
| 2014/0074090 A1* | 3/2014 | Lam | A61B 18/042 |
| | | | 606/49 |

* cited by examiner

SYSTEM AND METHOD FOR COLD PLASMA THERAPY

RELATED APPLICATIONS

This application claims the benefit of U.S. Provisional Application No. 61/492,167, filed Jun. 1, 2011, the entire contents of which are incorporated herein by reference.

BACKGROUND OF THE INVENTION

Field of the Invention

The present invention relates to tumor ablation. More particularly, the present invention relates to cold plasma ablation of cancerous tumors.

Background of the Related Art

Plasma is an ionized gas that is typically generated in high-temperature laboratory conditions. Recent progress in atmospheric plasmas has led to the creation of cold plasmas with ion temperature close to room temperature. Earlier studies demonstrated the non-aggressive nature of the cold plasma. After it was shown, albeit indirectly, that plasma can interact with organic materials without causing thermal/electric damage to the cell surface, several biological applications were examined. Low-temperature or cold plasmas have an increasing role to play in biomedical applications. The potential use in biomedical applications has driven the development of a variety of reliable and user-friendly plasma sources. There is still some controversy with respect to the mechanism of plasma-cell interaction. Some authors have expressed the opinion that ion species play the most important role in plasma-cell interactions by triggering intracellular biochemistry. Alternatively, others have suggested that neutral species play the primary role in some plasma-cell interaction pathways. Furthermore, the effects of various ion species may be highly selective; different species can have either "plasma killing" (such as O) or "plasma healing" (such as NO) effects. The role of other species, such as $O_3$ and OH, are not yet clear.

Even less clear is the nature of the interaction between cold plasmas and cancer tissue. Only limited research into the utility of cold plasma for cancer therapy has been performed. For the most part, these in-vitro studies are limited to skin cells and simple cellular responses to the cold plasma treatment. In addition, preliminary reports on plasma's in-vivo antitumor effect are reported. Recent studies have delineated cold plasma's effects on both the cellular and sub-cellular levels. On the cellular level, plasma effects include detachment of cells from the extracellular matrix and decreased migration velocity of cells. On the sub-cellular level, cell surface integrin expression is reduced.

SUMMARY OF THE INVENTION

The present invention is a device that uses cold plasma to treat cancerous tumors. The device has a gas supply tube with a delivery end. The gas supply tube is configured to carry a gas to the delivery end. A syringe is provided having an opening. The syringe is connected to the supply tube and configured to carry the gas to the opening. A first electrode is positioned inside said syringe, and a second electrode is positioned adjacent to the opening. The first and second electrodes excite the gas to enter a cold plasma state prior to being discharged from the opening of the syringe. An endoscopic tube can be used instead of the syringe. An exhaust tube can be provided to remove gas introduced into the body cavity by the cold plasma jet.

In another preferred embodiment, the present invention device for the treatment of target tissue. The device comprises a housing having a main body having a first port for admitting an electrode and a second port for admitting a gas, a neck extending from a distal end of the main body, the neck being narrower than the main body and having within it a channel having an exit away from the main body and a chamber within the main body, a first electrode extends from outside the main body through the first port into the chamber within the main body, a second electrode outside the neck surrounds the channel. A gas flowing into the housing through the second port, through the housing, and out the exit is excited into a cold plasma state by electrical energy applied to the first and second electrodes.

Both in-vitro and in-vivo studies revealed that cold plasmas selectively kill cancer cells. We show that a) cold plasma application selectively eradicates cancer cells in-vitro without damaging normal cells; and b) significantly reduces tumor size in-vivo. It is shown that ROS metabolism and oxidative stress responsive genes are deregulated. The development of cold plasma tumor ablation has the potential of shifting the current paradigm of cancer treatment and enabling the transformation of cancer treatment technologies by utilization of another state of matter.

These and other objects of the invention, as well as many of the intended advantages thereof, will become more readily apparent when reference is made to the following description, taken in conjunction with the accompanying drawings.

BRIEF DESCRIPTION OF THE FIGURES

For a more complete understanding of the present invention and the advantages thereof, reference is now made to the following description and the accompanying drawings, in which.

DETAILED DESCRIPTION OF THE PREFERRED EMBODIMENTS

In describing the preferred embodiments of the present invention illustrated in the drawings, specific terminology is resorted to for the sake of clarity. However, the present invention is not intended to be limited to the specific terms so selected, and it is to be understood that each specific term includes all technical equivalents that operate in a similar manner to accomplish a similar purpose.

Cold plasma is an ionized gas with ion temperature close to room temperature and can be used to selectively attack cancerous tissue without damaging normal cells and reduce tumor size in-vivo. The paper entitled "Cold Plasma Selectivity and the Possibility of a Paradigm Shift in Cancer Therapy," to M. Keider et al., British Journal of Cancer (2011) 105, pp. 1295-1301 which is part of the specification, discloses the use of cold plasma for cancer treatment.

Figure 1:
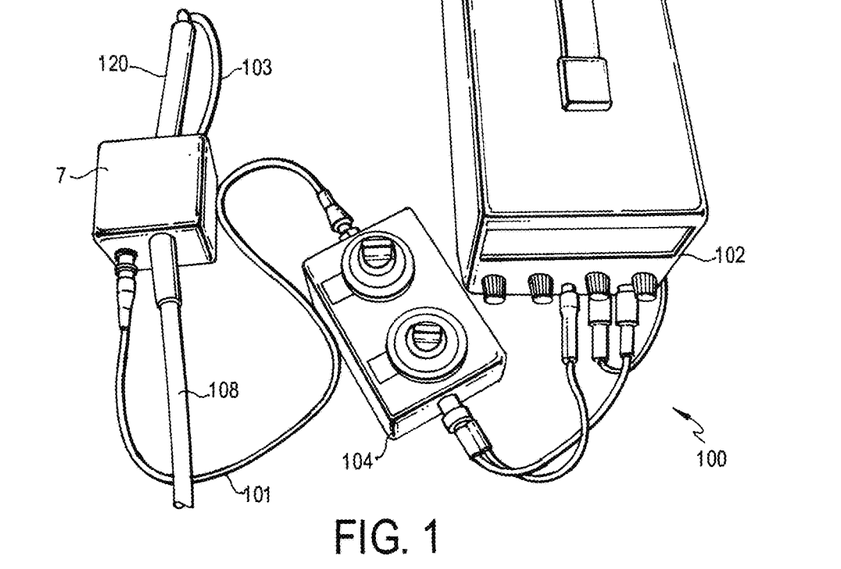
FIG. 1 shows a system in accordance with a preferred embodiment of the present invention.
Figure 2:
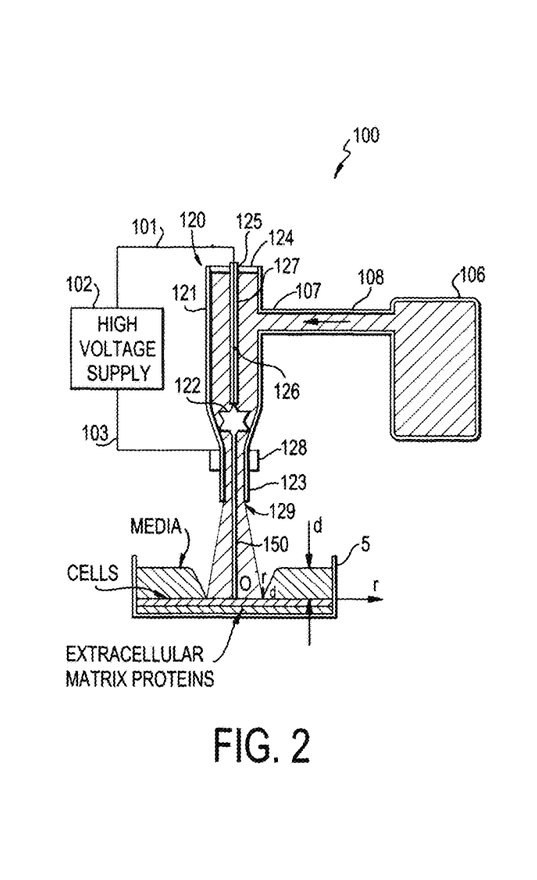
FIG. 2 shows an overall system in accordance with a preferred embodiment of the present invention connected with a gas tank.
Figure 3:
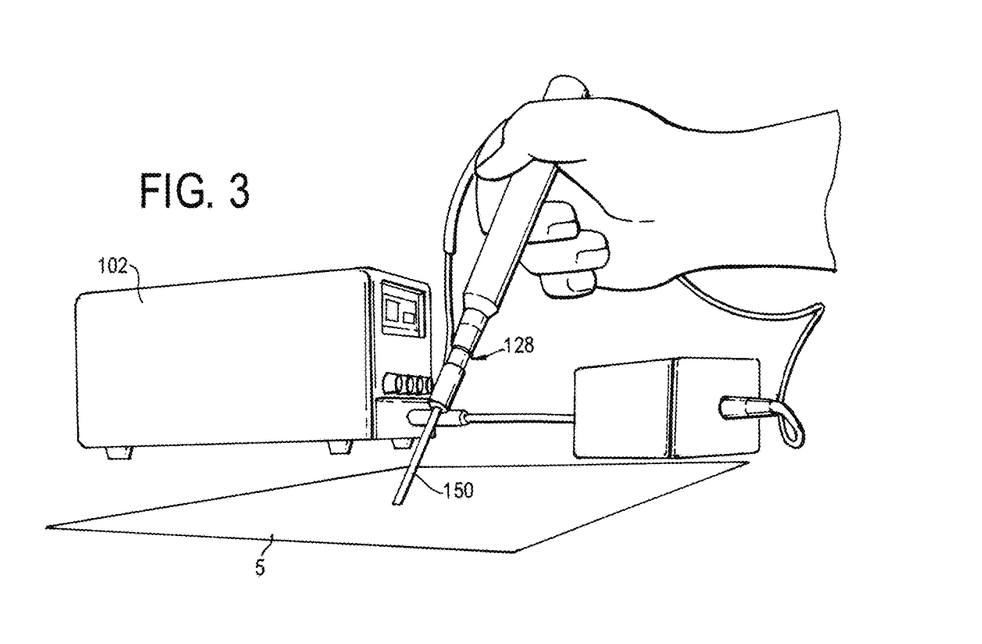
FIG. 3 is an image of the syringe emitting a cold plasma flow in accordance with a preferred embodiment of the present invention.

Turning to the drawings, FIGS. 1-3 show a cold plasma therapy system 100 in accordance with the invention. The system 100 includes a power supply 102, controller 104, gas source 106, and delivery mechanism 120.

In the embodiment shown in FIG. 2, the delivery mechanism 120 is an elongated syringe having a main body 121. The body 121 can be made by glass or a rigid plastic, but also can be made of a flexible material. A proximal end of the body 121 is sealed 124 and an opposite distal end has a discharge area 122. The distal discharge end 122 of the syringe body 121 has a narrowed neck 123 and a distal opening or nozzle 129. A central electrode 126 is located at the center of the body 121 at the interior of the body 121 at the central longitudinal axis of the syringe 120. The central electrode 126 enters the syringe 120 at the sealed proximal end of the body 121 and extends the length of the body 121 to approximately the discharge end 122. A sealing plug 124 (such as rubber) is located over the open end of the syringe 120 to prevent the gas from escaping from the inside of the syringe 120.

The electrode 126 is entirely surrounded by insulation 127 except at its distal end which is exposed and in contact with gas and plasma. The insulation allows the power to be focused at the exposed distal end to lead to the discharge at the end. The central electrode 126 and surrounding insulation 127, has a proximal end that extends to the outside of the syringe 120 through an opening 125 in the plug 124. The plug opening 125 forms a friction fit with the insulation 127, so that gas does not escape from the syringe 120. Thus, the central electrode 126 is positioned inside the body 121 of the syringe 120, except for the portion of the proximal end of the electrode 126 that extends into and through the plug 124. In this manner, the plug opening 125 holds the electrode 126 and insulation 127 in position within the syringe 120, with the distal end of the electrode 126 facing the distal nozzle 129 of the syringe body 121.

In addition, an annular outer ring electrode 128 is located about a portion of the narrow neck 123 at the outside of the syringe 120. The electrodes 126, 128 are high voltage electrodes. The central electrode 126 can be, for instance, a wire, and the insulation 127 can be a ceramic insulation. The power supply 102 is electrically connected to the electrodes 126, 128 and provides a high voltage supply to the electrodes 126, 128 through the cables 101, 103. The controller 104 regulates the voltage and frequency that is applied to the central electrode 126 and the ring electrode 128. An optional adapter 7 (FIG. 1) interfaces the delivery device 120 with high voltage transformer 102.

The gas source 106 is in gas communication with the delivery device 120 through a supply tube 108. The supply tube 108 is connected to a port 107 located in a side of the body 121 of the syringe 120, as shown in FIG. 2. The supply tube 108 can also be connected to the syringe 120 through the adapter 7, as shown in FIG. 1. The gas source 106 can be pressurized, so that gas travels through the supply tube 108 into the inside space of the syringe body 121. A separate gas controller (not shown) can be provided to control the flow rate of the gas in the supply tube 108, or the gas controller can be integrated with the controller 104. The gas then continues through the syringe 120 and exits the syringe 120 through the neck 123 and nozzle 129 at the discharge end 122 as a jet or stream flow 150.

As the gas enters the discharge area 122 and the neck 123 of the syringe 120, the electrodes 126, 128 excite the gas, thereby ionizing the gas to form a cold plasma. In the embodiment shown, the gas is Helium, though other gases such as Nitrogen may be used. Thus, as the gas is discharged out of the distal nozzle 129 of the syringe 120, it is a cold plasma. The cold plasma jet or stream flow 150 diffuses over time. In accordance with a preferred embodiment of the invention, the plasma is provided at a flow rate of 17 liters per minute, with the voltage supply being 5 kV and 30 kHz. At that configuration, the plasma will have a high ionization as it exits the syringe 120. Accordingly, the syringe 120 is preferably placed at a predetermined distance, which can be about 2 cm away from the target cells 5 being treated. The syringe 120 allows the plasma to be targeted at desired cancer cells in the skin to selectively eradicate the cancerous cells and reduce tumor size. The syringe 120 can be utilized, for instance, to treat any cancer type which is close to the skin and can be applied without surgery, such as breast, colon, lung, bladder, or oral. With surgery, the invention can be applied to any tumor. In accordance with an illustrative embodiment, the flow rate can be 10-17 liters/min., with a voltage of 2-5 kV and frequency of 30-35 KHz, and a nozzle 129 of 3-5 mm diameter and a distance between the central electrode 126 and the ring electrode 128 of 5-10 mm. The plasma preferably has a density of about $3 \times 10^{13}$ to $9 \times 10^{13}$ $cm^{-3}$, such as discussed in "Temporary-resolved measurement of electron density in small atmospheric plasmas," to Shashurin et al., Applied Physics Letters 96, 171502 (2010), which is hereby incorporated by reference.

At the predetermined distance, the plasma will have diffused to a desirable level. However, the intensity of the plasma will continue to decrease as the target area is moved further from the syringe 120, and the plasma will be essentially entirely dissipated at a distance of 5 cm from the syringe 120. The plasma is well collimated the entire length up to about 5 cm from the syringe 120. The plasma jet stream is discontinuous and represents a series of propagating plasma bundles.

It should be apparent, however, that other suitable settings can be utilized. Preferably, however, the power supply 102 has a voltage from about 2-5 kV with a frequency of about 30 kHz, and the gas has a flow rate of about 2-17 l/min.

Figures 4, 5:
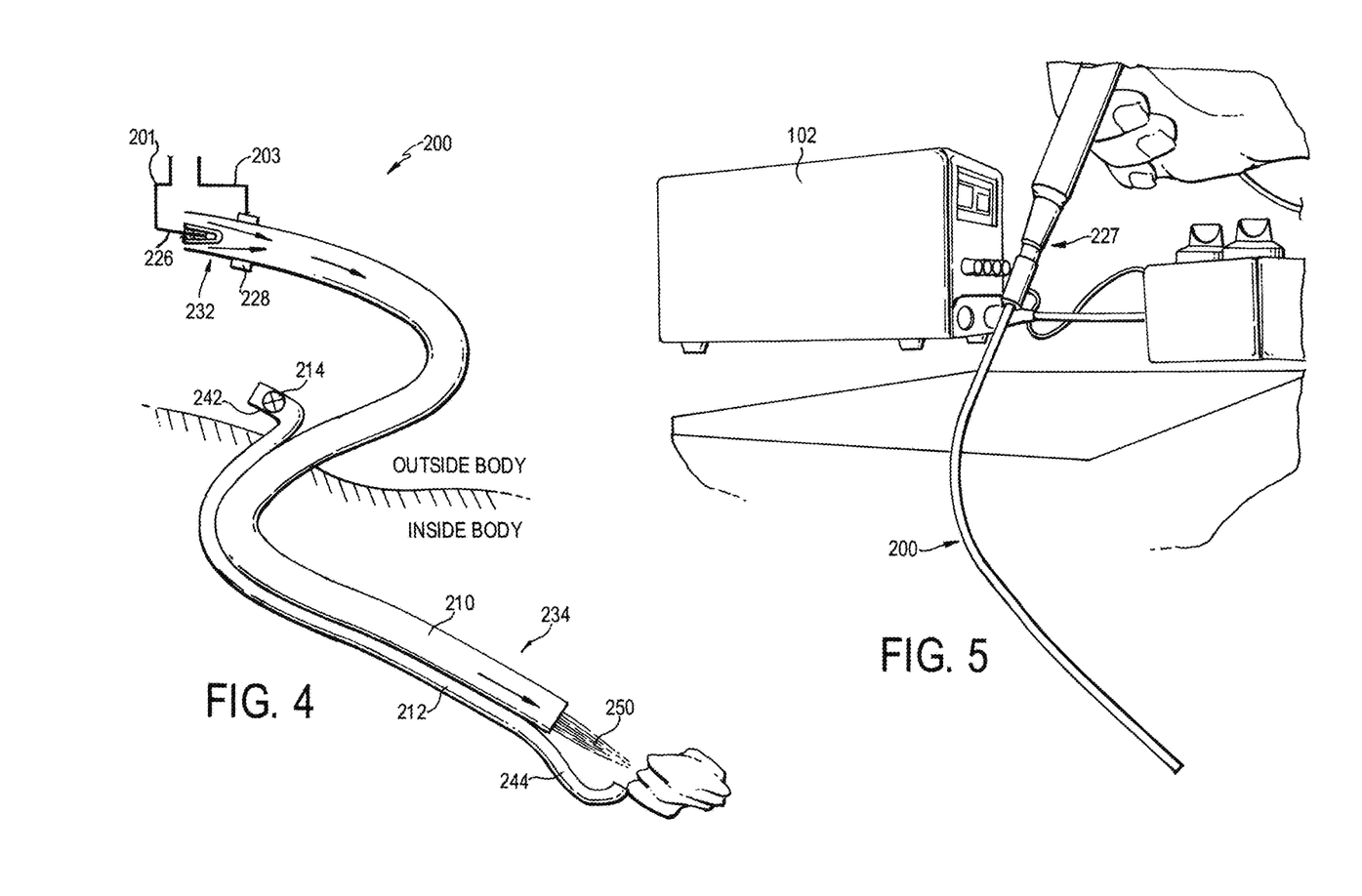
FIG. 4 is an alternative embodiment of the present invention having an endoscopic tube and an exhaust tube.
FIG. 5 shows the endoscopic tube attached to a power supply.

Turning to FIGS. 4-5, another embodiment of the invention is shown having a different delivery device. Here, the system has an endoscopic delivery device 200. The delivery device 200 includes a flexible elongated endoscopic tube 210, and a return or exhaust tube 212. A proximal or entry end 232 of the endoscopic tube 210 is connected to a gas storage tank, optionally through a gas regulator or controller. A central electrode 226 is located inside the endoscopic tube 210 at the entry end 232 of the endoscopic tube 210. An annular ring electrode 228 is located about the entry end 232 of the endoscopic tube 210 near the central electrode 226. The central electrode 226 is about 1-2 cm from the ring electrode 228. The cables 201, 203, deliver power from a power supply to the electrodes 226, 228.

A delivery end (or distal end) 234 of the endoscopic tube 210 is located opposite the entry end 232. The gas travels through the endoscopic tube 210 at a desired flow rate with a regulated pressure from the entry end 232 to the deliver end 234. In the process, the electrodes 226, 228 excite the gas at the entry end 232 to form a cold plasma which exits the delivery end 234 of the endoscopic tube 210 as a jet stream 250. The delivery end 234 can optionally have a nozzle to control the type of stream that is emitted from the endoscopic tube 210. The delivery end 234 allows the gas and plasma state helium to flow at a certain pressure so that the plasma/gas beam 250 can be moved and focused on cancer or precancerous lesions at a target site. Here, the site is in the upper and lower gastrointestinal tracts with an upper gastrointestinal endoscope 210 or colonoscope.

The distal end 234 of the endoscopic tube 210 is delivered to an internal site within a body (such as the gastrointestinal tracts, lungs or bladder in a human body) to treat cancerous at precancerous lesions at those sites. As shown in FIG. 4, the proximal end 232 remains outside of the patient's body so that the electric and gas can be delivered to the endoscopic tube 210. However, at an internal site within the patient's body, the gas from the plasma beam 250 may not have an easy way to be released from within the body and can become trapped in the confined space.

The exhaust tube 212 can optionally be provided, and have a pump or fan 214 or other mechanism that draws in the gas from the internal site. Thus, the exhaust tube 212 creates a vacuum flow by sucking out the excess gas from the body which is introduced by the endoscopic tube 210. The exhaust tube 212 is preferably connected to the endoscopic tube 210 in any suitable and conventional manner. The exhaust tube 212 can extend substantially parallel to the endoscopic tube 210 and any other manipulative/surgical tools attached to the endoscopic tube 210, so that the exhaust tube 212 can be introduced into the patient's body together with the endoscopic tube 210. The exhaust tube 212 has a proximal end 242 and a distal end 244.

The exhaust tube 212 can be located at any suitable distance from the endoscopic tube 210. Preferably, the very distal end 244 of the exhaust tube 212 has a curved hook shape. In addition, the exhaust tube 212 is preferably longer than the endoscopic tube 210 at the distal ends 234, 244, so that the distal end 244 of the exhaust tube 212 projects forward from the distal end 234 of the endoscopic tube 210 and is closer to the target. At the very distal end 234 of the endoscopic tube 210, the distal end 244 of the exhaust tube 212 curves outward away from the distal end 234 of the endoscopic tube 210 and the plasma jet 250, then curves back toward the target site. Thus, the exhaust tube 212 is located far enough away from the distal end 234 of the endoscopic tube 210 so that it does not interfere with the jet stream 250 emitted from the tube 210, but close enough to retrieve the gas.

However, the distal end 244 of the exhaust tube 212 need not extend beyond the distal end 234 of the endoscopic tube 210, and/or need not be curved. Rather, the very distal end 244 of the exhaust tube 212 can be substantially even with, or receded from, the very distal end 234 of the endoscopic tube 210.

The proximal end 242 of the exhaust tube 212 is retained outside the body so that the gas can be expelled, while the distal end 244 of the tube 212 is placed inside the patient's body to collect the gas.

Figure 6:
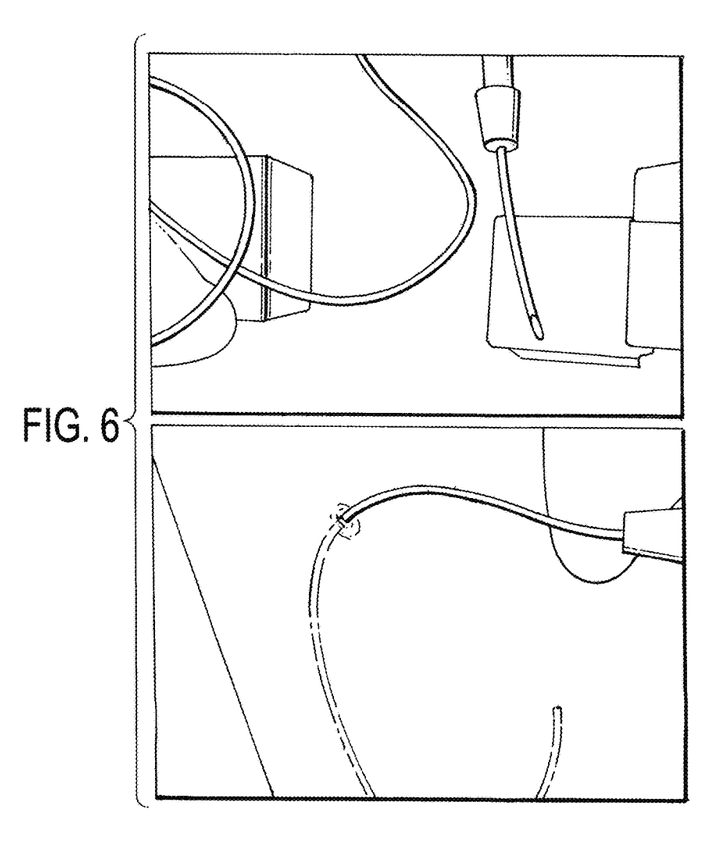
FIG. 6 shows delivery of the plasma.

The endoscope 210 can provide a camera or the like, as well as other suitable surgical tools or device, which facilitates introduction of the tube 210 and the exhaust tube 212 to the internal site and delivery of the plasma beam 250 to the target tissue at a predetermined desired distance. In addition, the endoscopic tube 210 can extend up to 1 meter or longer. The plasma does not diffuse very quickly inside the tube 210; but the voltage (approximately 10V) can be raised if necessary, to retain a desired plasma strength when it strikes the target. FIG. 6 shows delivery of the plasma through a 2 mm diameter flexible plastic endoscopic tube 210. It will be apparent that other suitable delivery devices can be utilized other than a syringe and endoscope, within the spirit and scope of the invention. In addition, while the electrodes 226, 228 are shown at the proximal end 232 of the endoscopic tube 210, they can instead be located at the distal end 234 of the endoscopic tube 210. In addition, other means can be utilized to create the plasma jet, and need not be limited to a central electrode and a ring electrode.

The syringe embodiment (FIGS. 1-3) and the endoscopic embodiment (FIG. 4) of the invention both include the concept of introducing a cold plasma jet to treat a tumor. The cold plasma source is equipped with a pair of high voltage (HV) electrodes, including a central electrode 126, 226 (which is isolated from the direct contact with plasma by ceramics) and an outer ring electrode 128, 228. The electrodes 126, 128, 226, 228 are connected to a secondary high-voltage resonant transformer with voltage of about 2-5 kV and a frequency of about 30 kHz with a helium flow rate of about 11 liters per minute. The visible plasma jet had a length of approximately 5 cm and is well collimated along the entire length. The plasma jet can be discontinuous and represents a series of propagating plasma bullets. The syringe embodiment is better suited to treat cancers at or close to the skin, whereas the endoscopic embodiment is better suited to treat internal tumors without surgery. When treating the open area (skin), the nozzle is placed at about 2 cm from the skin. Plasma can be delivered by propagating in the air to such distances and thus there is no need for an exhaust tube.

For in-vitro assays, we examined the Normal Human Bronchial Epithelial (NHBE) and the lung cancer (SW900) cell lines. Cold plasma treatments were carried out at high voltage in the range of 3-5 kV, helium flow in the range 10-20 L·min$^{-1}$, distance from plasma source to cells of about 1 cm and treatment durations of about 30 s.

Murine Melanoma Cells. B16-F10 melanoma cells were purchased from American Type Culture Collection (Manassas, Va.). Cells were cultured in D10 media (DMEM media containing 10% fetal calf serum, 1% penicillin/streptomycin, and 1% L-glutamine).

Primary bone marrow macrophages were directly harvested from the tibias and femurs of sacrificed mice. Cells were cultured in 30% L929 cell conditioned media (LCCM), re-fed on either day 2 or 3, and plated between days 6 and 9.

Flow Cytometry. Triplicate samples of $1\times10^4$ murine macrophages and B16-F10 melanoma cells were plated into 96 well plates with 100 μl of D10 media (Dulbecco's modified eagle's medium (DMEM) (Sigma-Aldrich)), supplemented with 10% fetal bovine serum, penicillin (100 IU/mL), streptomycin (100 μg/mL) (Sigma-Aldrich), and 1% L-Glutamine (Mediatech Inc Manassas, Va.)) per well. After cold plasma treatment, cells were collected and stained with fluorescein isothiocyanate (FITC)-conjugated Annexin V and 7-Aminoactinomycin D (7-AAD) obtained from BD Biosciences (San Jose, Calif.). Flow cytometry was performed using FACS Calibur (BDBioscience, San Jose, Calif.); results were analyzed using FlowJo software (Ashland, Oreg.).

In-Vivo Assays. B16 and subcutaneous bladder cancer tumors (SCaBER) cells of $2\times10^5$ B16 and SCaBER cells were subcutaneously injected into the right hind legs of 8 C57B16 mice (4 control and 4 treated) 10 nude mice (5 control and 5 treated) respectively. B16 tumors were treated with cold plasma once they were approximately 5 mm in maximum diameter. Control mice received no therapy after inoculation. All treated mice received 5 minutes of cold plasma treatment. Tumors were treated through the skin, no overlying incisions were made. Mice received one round of treatment only. Tumor volumes were calculated using the formula $V=0.52(X^2Y)$. Control and treatment mice were sacrificed when tumors reached a maximum diameter of 20 mm, if tumor bleeding or ulceration occurred, or if the mice appeared moribund.

The cold plasma jet was also applied to nude mice bearing subcutaneous bladder cancer tumors (SCaBER). We examined the mouse skin after 2 to 5 minutes cold plasma treatment to compare gross tissue damage to the skin before after treatment. We extracted RNA to perform gene expression analyses.

A gene expression profile of treated and untreated tumor was obtained using genome-wide HumanHT-12 v4 Expression BeadChip arrays (Illumina, San Diego, Calif.). Each array on the HumanHT-12 Expression BeadChip targets more than 25,000 annotated genes with more than 48,000 probes derived from the National Center for Biotechnology Information Reference Sequence (NCBI) RefSeq (Build 36.2, Rel 22) and the UniGene (Build 199) databases.

Total RNA was prepared as described in the RNeasy Mini Kit (Qiagen) with on-column DNase I digestion. All samples were processed at the Sidney Kimmel Comprehensive Cancer Center Microarray Core Facility at Johns Hopkins University, Baltimore. Briefly, 500 ng total RNA from each sample was amplified and labeled using the Illumina Total-Prep RNA Amplification Kit, AMIL1791 (Ambion, Austin, Tex.) as described in the instruction manual. All arrays were hybridized at 58° C. for 16-20 hours followed by wash and stain procedures according to the Whole-Genome Gene Expression Direct Hybridization Assay Guide (Illumina) Fluorescent signals were obtained by scanning with iScan System and data were extracted with Gene Expression Module 1.0.6 in GenomeStudio 1.0.2 with or without background subtraction.

Pathway and ontology analysis were performed to identify how the observed expression changes between treated and untreated tumor tissue alters cellular networks and signaling pathways. A list of RefSeq identifiers for up/down-regulated genes was uploaded to the Ingenuity Pathway Analysis program (Redwood City, Calif.), enabling exploration of gene ontology and molecular interaction. Each uploaded gene identifier was mapped to its corresponding gene object (focus genes) in the Ingenuity Pathways Knowledge Base. Core networks were constructed for both direct and indirect interactions using default parameters, and the focus genes with the highest connectivity to other focus genes were selected as seed elements for network generation. New focus genes with high specific connectivity (overlap between the initialized network and gene's immediate connections) were added to the growing network until the network reached a default size of 35 nodes. Non-focus genes (those that were not among our differentially expressed input list) that contained a maximum number of links to the growing network were also incorporated. The ranking score for each network was then computed by a right-tailed Fisher's exact test as the negative log of the probability that the number of focus genes in the network is not due to random chance. Similarly, significances for functional enrichment of specific genes were also determined by the right-tailed Fisher's exact test, using all input genes as a reference set.

Results are representative of three independent experiments. Error bars represent standard error of the mean (SEM). Statistical analysis was performed using GraphPad Prism 5 Software (La Jolla, Calif.). For in-vitro assays, one-way ANOVA with Bonferroni's post-test was performed to determine differences in viable cells both between all groups and between treatment groups and controls. For in-vivo survival, Kaplan-Meier curves were developed and Log-Rank (Mantel-Cox) testing was performed. For gene analyses, the ranking score for each network was computed by a right-tailed Fisher's exact test as the negative log of the probability that the number of focus genes in the network is not due to random chance. Similarly, significances for functional enrichment of specific genes were also determined by the right-tailed Fisher's exact test, using all input genes as a reference set.

For the proposed studies we utilized procedures detailed in a protocol approved by the Johns Hopkins Animal Care and Use Committee (Protocol # MO09M47) and Children's National Medical Center ACU committee (Protocol #198-12-06). All animals were subjected to strict supervision and veterinary care by the Division of Comparative Medicine at the Johns Hopkins University School of Medicine and the Research Animal Facility at the Children's National Medical Center. Animal care complied with Federal and State regulations regarding proper and humane treatment of animals.

Figure 7:
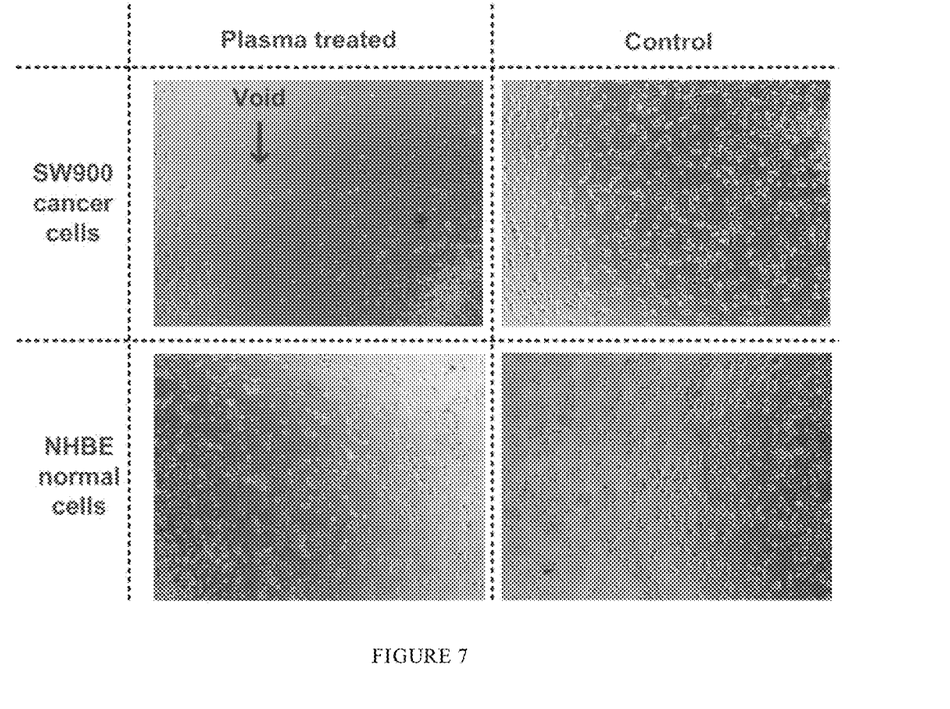
FIG. 7 shows the selectivity effect of plasma treatment: SW900 cancer cells were detached from the plate in the zone treated with plasma, while no detachment was observed in the treated zone for the normal NHBE cells.

Results for in-vitro Cold Plasma treatment to cell lines. A strong selective effect was observed, resulting 60-70% of SW900 cancer cells were detached from the plate in the zone treated with plasma, while no detachment was observed in the treated zone for the normal NHBE cells under same treatment conditions. Images of treated and untreated NHBE and SW900 cells are shown in FIG. 7. Plasma treatment leads to a significant reduction in SW900 cell count, while NHBE cell count is practically unchanged. Both murine macrophages and B16 melanoma cells were treated with the cold plasma device for 0, 30, 60, and 120 seconds. Annexin V and 7-AAD staining was performed for flow cytometry analysis at 24 and 48 hours after treatment.

A clear-dose response to cold plasma treatment is seen in the murine melanoma cells at both 24 and 48 hours (p<0.0001), while the treated murine macrophages do not differ from control at either 24 or 48 hours (p=0.1350 and 0.1630, respectively). These findings suggest that the cold plasma jet has a more selective effect on murine melanoma cells.

In order to determine the cold plasma effect in-vivo, we applied the cold plasma jet to nude mice bearing subcutaneous bladder cancer tumors (SCaBER). We examined the mouse skin after cold plasma treatment and did not see any damage to the skin after 2 to 5 minutes of treatment. Tumor models were treated by cold plasma. A single plasma treatment leads to tumor ablation with neighboring tumors unaffected. These experiments were performed on 10 mice with the same outcome. We found that tumors of about 5 mm in diameter are ablated after 2 minutes of single time plasma treatment while larger tumors decreased in size. Interestingly, ablated tumors did not grow back while partially affected tumors started growing back a week after treatment, although they did not reach the original size even after a 3 weeks after treatment.

We next evaluated the cold plasma device for in-vivo efficacy in a murine melanoma model. While tumors eventually recurred, a single transcutaneous cold plasma treatment induced ablation of the tumor through the overlying skin. Tumor growth rates were markedly decreased after cold plasma treatment. Notably, this resulted in a markedly improved survival in the treatment group (p=0.0067), with a median survival of 33.5 versus 24.5 days.

Skin temperature is not increased by Cold Plasma treatment. The skin temperature during plasma treatment was measured using an infrared thermometer (Traceable, Model#4470) to assess whether the cold plasma effect on cancer tissue is associated with thermal damage. Cold plasma treatment produced an increase in skin temperature of approximately 2° C. above room temperature, which is below the temperature needed for thermal damage.

Gene expression analysis of Cold Plasma treated bladder cancer tumor tissue demonstrates alteration in various pathways. The beta values of all probes on the Illumina BeadChip arrays were subjected to log 10 transformation and then normalized to the average in order to generate a heatmap of selected genes based on unsupervised hierarchical clustering with the SPOTFIRE® software (Somerville, Mass.). The clustering was based on the unweighted average method using correlation as the similarity measure and ordering by average values. The color red was selected to represent up regulated genes and the color green to represent down-regulated genes. Genes were selected for clustering if they were four times up regulated or downregulated after treatment with cold plasma. The most up regulated genes and the most downregulated genes after cold plasma treatments and the genes that were differentially expressed after cold plasma treatment, are discussed in "Cold plasma selectivity and the possibility of a paradigm shift in cancer therapy," to Keidar, et al., British Journal of Cancer (2011) 105, 1295-1301 (http://www.nature.com/bjc/journal/v105/n9/full/bjc2011386a.html), which is hereby incorporated by reference.

Differences between genes that were up- or down-regulated in treated or untreated cells were analyzed for biological significance using Geneontology (Spotfire®) and Ingenuity Pathway Analysis (IPA®). Differences in gene expression were found to be associated with pathways intimately related to: cell adhesion; cell proliferation; growth regulation; and cell death ($p<0.05$).

The top associated network functions in IPA, shown in Supplementary Table 2, are pathways directly related to organismal injury and abnormalities: cellular development, cell signaling, cellular movement, dermatological diseases and conditions, cell death, and inflammatory response ($p<0.05$).

Several genes associated with the apoptotic and oxidative stress pathways in were deregulated in tumors treated with cold plasma. Details of the upregulated and down-regulated networks are presented in the Keidar publication referenced above.

The invention demonstrates potent effects of cold plasma treatment on cancerous tissue both in-vitro and in-vivo. Previous research has offered several potential mechanisms for cold plasma's effect, including development of reactive oxygen species (ROS), reactive nitrogen species (RNS), charged particles, heat, pressure gradients, and electrostatic and electromagnetic fields. Notably, plasma has minimal impact on ambient cellular conditions. For instance, media pH levels remain unchanged after treatment, and our study confirms that thermal effects associated with cold plasma are negligible. Beyond the direct external influence of the jet, cold plasma may induce living cells to produce their own ROS/RNS. Thus, these preliminary results suggest that multiple pathways involved in cancer processes, including cell adhesion, cell proliferation, growth regulation, and cell death, are selectively deregulated by cold plasma treatment in cancer cells. Some of these pathways may likely be responsible for tumor ablation. Perhaps consequently, we further demonstrate induction of cellular apoptosis in treated cells, as manifested by both expression of cell-surface markers and gene expression, confirming results of previous studies. Most importantly, these findings are translated to in-vivo models of cancer therapy, with marked reductions in tumor volumes and improved survival.

Given these findings, we believe that cold plasma represents a promising new adjunct for cancer therapy, offering the ability to directly target and selectively kill neoplastic tissue. Notably, our plasma-jet device provides a method for practical administration of this cancer therapy. Plasma therapy could potentially target internal malignancies via an endoscopic delivery system, thus enabling this technology to serve as either a stand-alone treatment option or, more realistically, as an adjuvant to existing therapies.

In summary, this proof-of-principle study shows new in-vitro and in-vivo response of cancer cells upon treatment with cold plasma jets. These very surprising preliminary results suggest that the cold plasma jet can selectively ablate some cancer cells (such as melanoma and bladder), while leaving their corresponding normal cells essentially unaffected. The two best known cold plasma effects, plasma-induced apoptosis and the decrease of cell migration velocity can have important implications in cancer treatment by localizing the affected area of the tissue and by decreasing metastasic development. Moreover, the selective effect of cold plasma on different cell types suggest that it is possible to find the right conditions with plasma treatment affecting only cancer cells, while leaving normal cells essentially unharmed. Finally, mid-sized tumors in nude mice were destroyed after a 2 minute single time treatment by cold plasma without thermal damage. As such, we expect that the development of cold plasma treatment will cause a paradigm shift in cancer therapy.

The following documents are incorporated herein by reference: (1) Fridman A (2008) Plasma Chemistry. Cambridge University Press: Cambridge; (2) Fridman G, Friedman G, Gutsol A, Shekhter A B, Vasilets V N, and Fridman A, (2008) Applied Plasma Medicine", Plasma Processes Polym. 5: 503-533; (3) Stoffels E, Flikweert A J, Stoffels W W, and Kroesen G M W (2002) Plasma needle: a non-destructive atmospheric plasma source for fine surface treatment of (bio)materials, Plasma Source Sci. Technol. 11: 383; (4) Stoffels E, Sakiyama Y and Graves D (2008) Cold atmospheric plasma: charged species and their interaction with cells and tissues, IEEE Trans. Plasma Sci. 36: 1441; (5) Laroussi M and Lu X (2005) Room-temperature atmospheric pressure plasma plume for biomedical applications, Appl. Phys. Lett. 87: 113902-113904; (6) Kong M G, Kroesen G, Morfill G, Nosenko T, Shimizu T, van Dijk J and Zimmermann J L (2009) Plasma medicine: an introductory review, New Journal of Physics 11: 115012; (7) Becker K H, Schoenbach K H and Eden J G (2006) Microplasmas and applications, J. Phys. D: Appl. Phys. 39: R55; (8) Morfill G E, Shimizu T, Steffes B and Schmidt H U (2009) Nosocomial infections—a new approach towards preventive medicine using plasmas, New Journal of Physics 11: 115019; (9) Stoffels E, Kieft I E, Sladek R E J, van den Bedem L J M, van der Laan E P, Steinbuch M (2006) Plasma needle for in-vivo medical treatment: recent developments and perspectives, Plasma Sources Sci. Technol. 15: 5169; (10) Fridman G, Dobrynin D, Kalghatgi S, Brooks A, Friedman G, Fridman A (2009) Physical and Biological Mechanisms of Plasma Interaction with Living Tissue, 36th Inter. Con. Plasma Science, San Diego, May 30-Jun. 5, 2009; (11) Kalghatgi S, Fridman A, Friedman G, Morss-Clyne A (2009) Non-Thermal Plasma Enhances Endothelial Cell Proliferation Through Fibroblast Growth Factor-2 Release, 36th Inter. Con. Plasma Science, San Diego, May 30-Jun. 5, 2009; (12) Kong M (2009) Plasma Medicine—Opportunities and Challenges for Science and Healthcare, Plenary Talk, 36th Inter. Con. Plasma Science, San Diego, May 30-Jun. 5, 2009; (13) Georgescu N and Lupu A R (2010) Tumoral and Normal Cells Treatment With High-Voltage Pulsed Cold Atmospheric Plasma Jets, IEEE Trans. Plasma Sci. 38: 1949-1956; (14) Zirnheld J L, Zucker S N, DiSanto T M, Berezney R and Etemadi K (2010) Nonthermal Plasma Needle: Development and Targeting of Melanoma Cells, IEEE Trans. Plasma Sci. 38: 948-952; (15) Kim J Y, Kim S O, Wei Y, and Li J, (2010) Flexible cold microplasma jet using biocompatible dielectric tubes for cancer therapy, Applied Physics Letters, 96: 203701; (16) Vandamme M, Robert E, Pesnel S, Barbosa E, Dozias S, Sobilo J, Lerondel S, Pape A L, Pouvesle J M (2010) Antitumor Effect of Plasma Treatment on U87 Glioma Xenografts: Preliminary Results, Plasma Proc. Polymers 7: 264-273; (17) Shashurin A, Keidar M, Bronnikov S, Jurjus R A, Stepp M A (2008) Living tissue under treatment of cold plasma atmospheric jet, Appl. Phys. Lett. 92: 181501; (18) Shashurin A, Stepp M A, Hawley T S, Pal-Ghosh S, Brieda L, Bronnikov S, Jurjus R A, Keidar M (2010) Influence of cold plasma atmospheric jet on integrin activity of living cells, Plasma Process. Polym. 7: 294-300; (19) Furchgott R F (1999) Endothelium-Derived Relaxing Factor: Discovery, Early Studies, and Identification as Nitric Oxide (Nobel Lecture) Angew. Chem. Int. Ed. 38: 1870; (20) Volotskova O, Shashurin A, Stepp M A, Pal-Ghosh S and Keidar M (2010) Plasma-controlled cell migration: localization of cold plasma-cell interaction region", Plasma Medicine 1: 83-92; and (21) Kieft I E, Kurdi M, Stoffels E (2006) Reattachment and Apoptosis After Plasma-Needle Treatment of Cultured Cells, IEEE Trans. Plasma Sci. 34: 1331-1336.

The description and drawings of the present invention provided in the paper should be considered as illustrative only of the principles of the invention. The invention may be configured in a variety of ways and is not intended to be limited by the preferred embodiment. For instance, although the invention has been described to treat cancerous tumors, it can be utilized for other applications. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A device for the treatment of target tissue comprising:
a housing comprising:
  a main body having a first port for admitting an elongated electrode and a second port for admitting a gas;
  a neck extending from a distal end of said main body, said neck being narrower than said main body and having within it a channel having an exit away from said main body; and
  a discharge area within said main body between said neck and said second port;
an elongated electrode extending through said first port and having a proximal end outside of said main body and a distal end in said discharge area within said main body;
a ring electrode outside said neck surrounding said channel;
wherein said elongated electrode and said ring electrode are configured to connect to a secondary high-voltage resonant transformer; and
wherein said elongated wire and said ring electrode are configured to excite a gas flowing into said housing through said second port, through said housing, and out said exit into a cold plasma state by RF electrical energy.

2. The device of claim 1, further comprising:
a gas source connected to said second port, wherein the gas supply provides gas at a flow rate of 10-17 liters/min.; and
secondary high-voltage resonant transformer connected to the inner central electrode and the outer electrode, wherein the secondary high-voltage resonant transformer.

3. The device of claim 1, further comprising a suction tube having a distal end positioned adjacent to a distal end of said neck.

4. The device of claim 1, further comprising a nozzle located at a distal end of said neck, said nozzle being configured to discharge a gas in a cold plasma state.

5. The device of claim 1, wherein the distal end of said neck has a reduced size.

6. The device of claim 1, further comprising a gas source connected to said second port, wherein the gas source contains gas that has a density of $3\times10^{13}$ to $9\times10^{13}$ cm$^{-3}$ when in a cold plasma state.

7. A device for treatment of target tissue, comprising:
a gas supply tube having a delivery end and an entry opening, said gas supply tube configured to carry a gas and cold plasma to the delivery end;
a syringe having an opening, said syringe connected to the gas supply tube and configured to carry the gas to the opening;
a first electrode positioned inside said syringe; and
a second electrode positioned outside the syringe adjacent to the opening in the syringe;
wherein said first and second electrodes are configured to connect to a secondary high-voltage resonant transformer and are configured to excite gas flowing through the syringe to enter a cold plasma state prior to being discharged from the opening of said syringe by RF electrical energy.

8. The device of claim 7, further comprising a nozzle at the syringe opening.

9. A method for treatment of target tissue, the method comprising:
providing gas through a delivery device having an internal first electrode and a second external electrode, said first and second electrodes being connected to a secondary coil of a transformer;
exciting the gas in the delivery device to a cold plasma state with high frequency energy from said secondary coil of said transformer; and
discharging the gas in the cold plasma state from the delivery device as a stream.

10. The method of claim 9, further comprising the step of applying the stream to cancerous or precancerous cells of a body.

11. The method of claim 9, further comprising selectively treating cancer cells with the cold plasma.

12. The method of claim 11, wherein the target tissue comprises lung, bladder or skin tissue.

13. The method of claim 12, wherein the target tissue comprises a tumor having a diameter of 5-10 mm, and the gas in the cold plasma state completely ablates the target tissue in a single treatment.

* * * * *